United States Patent [19]
Moriya

[11] Patent Number: 5,748,320
[45] Date of Patent: May 5, 1998

[54] WIRING PATTERN LINE WIDTH MEASURING APPARATUS

[75] Inventor: Kazuo Moriya, Ageo, Japan

[73] Assignee: Mitsui Mining & Smelting Co. Ltd., Tokyo, Japan

[21] Appl. No.: 794,393

[22] Filed: Feb. 6, 1997

[30] Foreign Application Priority Data

Feb. 16, 1996 [JP] Japan ................................. 8-052534

[51] Int. Cl.$^6$ ................................................. G01B 11/00
[52] U.S. Cl. ................................. 356/385; 250/559.24
[58] Field of Search ............................. 356/384, 385, 356/429, 430, 375; 250/559.24, 559.34

[56] References Cited

U.S. PATENT DOCUMENTS

| | | | |
|---|---|---|---|
| 4,744,662 | 5/1988 | Suto et al. | 356/384 |
| 4,908,656 | 3/1990 | Suwa et al. | 356/401 |
| 5,048,966 | 9/1991 | Schram | 356/384 |
| 5,621,218 | 4/1997 | Tanaka | 250/559.34 |

Primary Examiner—Frank G. Font
Assistant Examiner—Zandra V. Smith
Attorney, Agent, or Firm—Kubovcik & Kubovcik

[57] ABSTRACT

An apparatus for measuring the line widths of a wiring pattern obtained by etching a metal foil includes a first illumination means for illuminating the wiring pattern from one side with a light beam having a first wavelength, a second illumination means for illuminating the wiring pattern from the other side with a light beam having a second wavelength which is different from the first wavelength, and a measuring means for obtaining information of a line width by the light beam having the first wavelength and a line width by the light beam having the second wavelength, on the basis of the light beams having the first and second wavelengths which advance at the same time point from the wiring pattern simultaneously illuminated by the first and second illumination means to said the other side. The wiring pattern may be repetitive patterns on a moving tape carrier. In that case, the first and second illumination means output the light beams having the first and second wavelengths as flashes, respectively, every time each repetitive pattern reaches a predetermined measurement position.

8 Claims, 2 Drawing Sheets

WIRING PATTERN LINE WIDTH MEASURING APPARATUS

BACKGROUND OF THE INVENTION

1. Field of the Invention

The present invention relates to an apparatus for measuring the line width of a wiring pattern obtained by etching a metal foil, e.g., a wiring pattern on a tape carrier (TAB tape).

2. Prior Art

Generally, a lead line pattern for TAB (Tape Automated Bonding) is formed by etching a copper foil sticked on a base film of Kapton, polyimide, or the like. The sectional shape of each lead line of the resultant wiring pattern has a trapezoidal shape, as shown in FIG. 3. A width Wt of the upper portion (top) of the lead line is different from a width Wb of the lower portion (bottom). To manufacture a TAB tape always having a predetermined shape, each of the two widths must be uniform. Therefore, it is important to measure the two widths and inspect whether each width is uniform.

In the conventional measurement, as shown in FIG. 2, the upper surface of a TAB tape 1 is illuminated by illumination means 5a, and the image of the TAB tape 1 is observed from the upper surface side through an image pickup means 4a, thereby measuring the width of the upper portion of the lead line. At the same time, the lower surface of the TAB tape 1 is illuminated by illumination means 5b, and the image of the TAB tape 1 is observed from the lower surface side through an image pickup means 4b, thereby measuring the width of the lower portion of the lead line.

However, according to this prior art, the upper surface and the lower surface are substantially measured by different units. Therefore, a long time is required for measurement. In addition, when the TAB tape is traveling, and the identical lead lines respectively of the repetitive wiring patterns of the TAB tape are to be measured, matching between the units and matching of the measurement positions and measurement timings are needed.

SUMMARY OF THE INVENTION

It is an object of the present invention to provide a wiring pattern line width measuring apparatus with a simple arrangement, which can easily and quickly measure the line widths of the upper and lower portions of a lead line. It is another object of the present invention to provide a wiring pattern line width measuring apparatus which can easily measure said line widths of the identical lead lines respectively of moving repetitive wiring patterns.

In order to achieve the above objects, according to the present invention, there is provided a wiring pattern line width measuring apparatus which measures the line widths of a wiring pattern obtained by etching a metal foil, comprising first illumination means for illuminating the wiring pattern from one side with a light beam having a first wavelength, second illumination means for illuminating the wiring pattern from the other side with a light beam having a second wavelength which is different from the first wavelength, and measuring means for obtaining information of a line width by the light beam having the first wavelength and information of a line width by the light beam having the second wavelength, on the basis of the light beams having the first and second wavelengths which advance from the wiring pattern simultaneously illuminated by the first and second illumination means to said other side at the same time point.

The wiring pattern is formed on, e.g., a tape carrier, and the light beam having the first wavelength has a wavelength which enable the light to be easily transmitted through the tape carrier. As the measuring means, a device which has a color TV camera, and obtains the information of the line width by the light beam having the first wavelength on the basis of image data obtained by one of the image pickup devices for respective colors of the TV camera and obtains the information of the line width by the light beam having the second wavelength on the basis of image data obtained by another color image pickup device can be used.

When the wiring pattern comprises repetitive patterns on a moving tape carrier, as the first and second illumination means, devices which output the light beams having the first and second wavelengths as flashes every time each repetitive pattern reaches a predetermined measurement position can be used. In this case, the line widths and the accurate position information about each measured line can be simultaneously obtained.

DESCRIPTION OF THE PREFERRED EMBODIMENT

Figure 1:
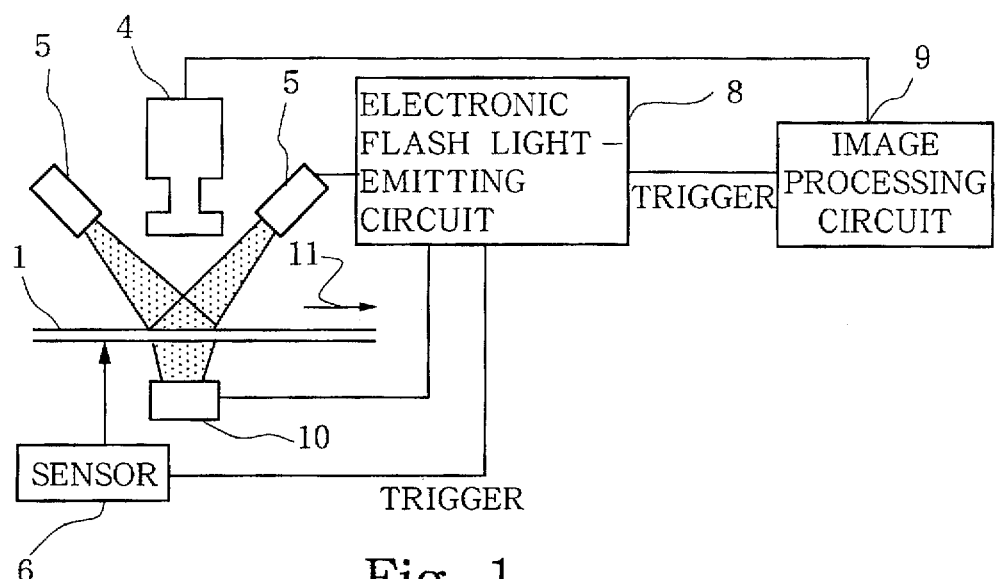
FIG. 1 is a block diagram showing the arrangement of a wiring pattern line width measuring apparatus according to an embodiment of the present invention.
Figure 2:
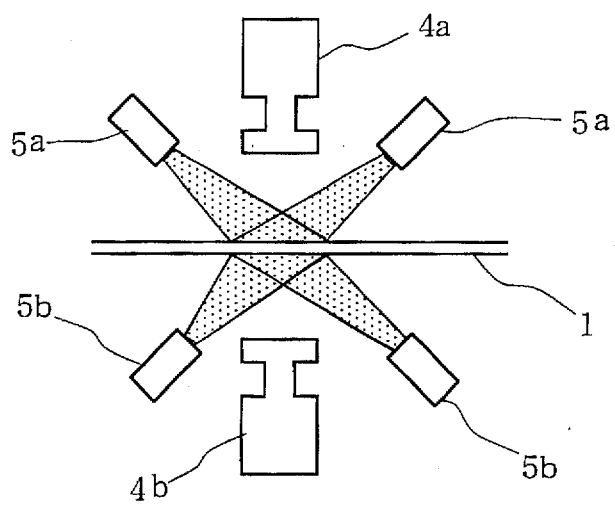
FIG. 2 is a view showing the arrangement of a conventional wiring pattern line width measuring apparatus.
Figure 3:
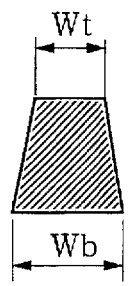
FIG. 3 is a sectional view showing the sectional shape of a lead line as a line width measurement target.

FIG. 1 is a block diagram showing the arrangement of a wiring pattern line width measuring apparatus according to an embodiment of the present invention. As shown in FIG. 1, this apparatus measures the line widths of a wiring pattern obtained by etching a copper foil on a TAB tape 1 and comprises a first electronic flash light-emitting device 10 for illuminating the wiring pattern from the lower side of the TAB tape 1 with a light beam having a first wavelength, second electronic flash light-emitting devices 5 for illuminating the wiring pattern from the upper side of the TAB tape 1 with light beams having a second wavelength, a color TV camera 4 for obtaining the information of a line width by the light beam having the first wavelength and a line width by the light beams having the second wavelength, on the has is of the light beams having the first and second wavelengths which advance from the wiring pattern simultaneously illuminated by the first and second electronic flash light-emitting devices 10 and 5 to the upper side of the TAB tape 1 at the same time point, and an image processing unit 9 connected to the color TV camera 4.

Figure 4:
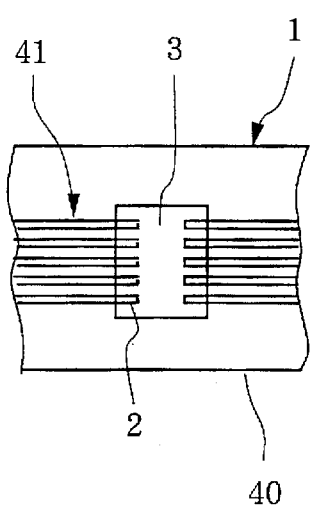
FIG. 4 is a view showing the device hole portion of a TAB tape.

As shown in FIG. 4, the TAB tape 1 has a wiring pattern 41 which is formed by sticking a copper foil on a Kapton or polyimide film 40 and etching the copper foil. As the electronic flash light-emitting device 10, a device for illuminating, as the light beam having the first wavelength, a light beam having a wavelength longer than that of red light (red to near infrared light), which is easily transmitted through the film 40 is used. As the electronic flash light-emitting device 5, a device for illuminating a blue or green light beam is used.

The image processing unit 9 performs image processing to obtain the line width by the light beam having the first wavelength on the basis of image data obtained by a red image pickup device of the respective color image pickup devices of the camera 4, and also performs image processing to obtain the line width by the light beam having the second wavelength on the basis of image data obtained by a blue or green image pickup device.

The wiring pattern 41 comprises repetitive patterns repeated at every device hole 3 on the TAB tape 1 which moves in a direction indicated by an arrow 11. Every time a repetitive pattern with a device hole 3 at its center reaches a predetermined measurement position, the first and second electronic flash light-emitting devices 10 and 5 are driven by an electronic flash light-emitting circuit 8 and emit the light beams having the first and second wavelengths as flashes, respectively. A trigger signal for this light emission is supplied from a sensor 6. The sensor 6 detects the sprocket holes or device holes of the TAB tape 1, or marks or the like formed on the TAB tape 1 in advance for position detection, and outputs the trigger signal to the electronic flash light-emitting circuit 8 every time each repetitive pattern reaches the measurement position.

In this arrangement, when a certain repetitive pattern or the TAB tape 1 reaches the measurement position, the sensor 6 outputs a trigger signal. The electronic flash light-emitting circuit 8 drives the electronic flash light-emitting devices 10 and 5 in accordance with this trigger signal. The electronic flash light-emitting device 10 emits a red light beam, and each electronic flash light-emitting device 5 emits a blue light beam (or a green light beam). The respective illumination light beams illuminate the TAB tape 1 from the lower and upper sides at the measurement position. At the same time, the electronic flash light-emitting circuit 8 outputs a trigger signal for image data reception to the image processing unit 9.

The red light beam is transmitted through the film from the lower side of the TAB tape 1 to the upper side of the TAB tape 1, captured by the camera 4, and formed into an image on the red image pickup device through a filter, though the red light beam is partially shielded by the lead line of the wiring pattern. The red image pickup device of the camera 4 outputs image data corresponding to the line width of the lower portion of the lead line. On the other hand, the blue light beam (or the green light beam) is reflected by the TAB3 tape 1 to the upper side, partially captured by the camera 4, and formed into an image on the blue image pickup device through a filter. The blue image pickup device outputs image data including image information corresponding to the line width of the upper portion of the lead line.

The image processing unit 9 receives the red image data and blue image data in accordance with the trigger signal from the electronic flash light-emitting circuit 8 and performs image processing to obtain the line widths of the lower and upper portions of the lead line. Consequently, line widths Wb and Wt of the lower and upper portions of the lead line and the ratio of these line widths can be obtained together with the accurate position information of the lead line.

When the line width of a portion on the film of the TAB tape 1 need not be measured, and the line width of only an inner lead portion 2 projecting in the device hole 3 of the TAB tape 1, as shown in FIG. 4, is to be measured, the light beam having the first wavelength need not have a wavelength which enable the light to be easily transmitted through the film. More specifically, the light beam having the first wavelength and that having the second wavelength may have such wavelengths that the light beams can be separated from each other by a filter or the like.

As described above, according to the present invention, the line widths of the upper and lower portions of the wiring pattern can be easily and quickly measured. The arrangement for this operation is relatively simple. For the wiring pattern of a moving TAB tape, the Line widths and accurate position information of the pattern can be simultaneously obtained by combining position detection of the pattern and illumination by electronic flash light emission synchronized with the position detection.

What is claimed is:

1. A wiring pattern line width measuring apparatus which measures the line widths of a wiring pattern obtained by etching a metal foil, comprising:

first illumination means for illuminating said wiring pattern from one side with a light beam having a first wavelength;

second illumination means for illuminating said wiring pattern from the other side with a light beam having a second wavelength which is different from the first wavelength; and measuring means for obtaining information of a line width by the light beam having the first wavelength and information of a line width by the light beam having the second wavelength, on the basis of the light beams having the first and second wavelengths which advance, at the same time point, in the direction from said wiring pattern simultaneously illuminated by said first and second illumination means to said other side.

2. An apparatus according to claim 1, wherein said wiring pattern is formed on a tape carrier, and the light beam having the first wavelength has a wavelength which enable the light beam to be easily transmitted through said tape carrier.

3. An apparatus according to claim 1, wherein said measuring means has color image pickup means, and obtains the information of the line width by the light beam having the first wavelength on the basis of image data obtained by one of image pickup devices for respective colors of said color image pickup means and obtains the information of the line width by the light beam having the second wavelength on the basis of image data obtained by another image pickup device.

4. An apparatus according to claim 1, wherein said wiring pattern comprises repetitive patterns on a moving tape carrier, and said first and second illumination means output the light beams having the first and second wavelengths as flashes every time each repetitive pattern reaches a predetermined measurement position.

5. An apparatus according to claim 4, further comprising means for detecting predetermined shapes on said tape carrier and outputting a trigger signal every time the repetitive pattern reaches the predetermined measurement position, and wherein said first and second illumination means output the light beams having the first and second wavelengths in accordance with the trigger signal.

6. An apparatus according to claim 5, wherein said measuring means has color image pickup means obtains the information of the line width by the light beam having the first wavelength on the basis of image data obtained by one of image pickup devices for respective colors of said color image pickup means, obtains the information of the line width by the light beam having the second wavelength on the basis of image data obtained by another image pickup device, and for that purpose, receives the image data obtained by said one of image pickup devices and the image data obtained by said another image pickup device in accordance with the trigger signal to perform image processing of both image data.

7. An apparatus according to claim 1, wherein said measuring means obtains the information of a line width of a lower portion of said wiring pattern by the light beam having the first wavelength, and obtains the information of a line width of an upper portion of said wiring pattern by the light beam having the second wavelength.

8. An apparatus according to claim 4, wherein said measuring means obtains information associated with a position of said wiring pattern on the basis of the light beams having the first and second wavelengths.

* * * * *